United States Patent [19]
Elliott et al.

[11] 3,960,142
[45] June 1, 1976

[54] AIR FLOW TO PRESSURE DIFFERENTIAL TRANSDUCER FOR PNEUMOTACHOGRAPHY

[75] Inventors: Stanley E. Elliott, San Bruno; Jack H. Shore, San Rafael, both of Calif.

[73] Assignee: The Institutes of Medical Sciences, San Francisco, Calif.

[22] Filed: Dec. 2, 1974

[21] Appl. No.: 528,600

[52] U.S. Cl............................ 128/2.08; 73/205 R; 73/206
[51] Int. Cl.²........................................ A61B 5/08
[58] Field of Search................. 128/2.08, 2.07, 2 C, 128/DIG. 29; 272/57 F; 73/205 R, 205 D, 205 L, 206

[56] References Cited
UNITED STATES PATENTS

| | | | |
|---|---|---|---|
| 3,611,801 | 10/1971 | Paine | 128/DIG. 29 |
| 3,643,652 | 2/1972 | Beltran | 128/2.08 |
| 3,718,135 | 2/1973 | Diamond | 128/2.08 |
| 3,797,479 | 3/1974 | Graham | 128/2.08 |

*Primary Examiner*—Robert W. Michell
*Assistant Examiner*—Lee S. Cohen
*Attorney, Agent, or Firm*—Townsend and Townsend

[57] ABSTRACT

A pneumotachograph having an improved air flow to pressure differential transducer is disclosed for producing a pressure differential during inspiration and expiration of respirative air to and from a hospital patient. Typically, the air flow to pressure differential transducer is attached to endotracheal tubing between the patient's trachea and the respirator valve. Specifically, the transducer provides the endotracheal tube with an enlarged and typically cylindrical volume having offset air passages communicating to the endotracheal tube. The unit area of the measuring chamber is greater than the unit area of the communicated endotracheal tubing and is typically cylindrical with respect to such tubing. Likewise, the area of the communicated endotracheal tube is preferably less than one quarter the cross-sectional area of the chamber. The endotracheal tubings are preferably offset so that their respective air flows are not in line and the generated air flow interior of the volume is turbulent but not circuitous. Both the communicated endotracheal tubings are provided with manometer taps substantially normal to the path of fluid flow therein so that pressure differential and not velocity head of the fluid flow is measured. The manometer taps are communicated to a differential pressure transducer. The output of this transducer passes to a linearization circuit to produce a measure of intake and outflow during the patient's respective inspiration and expiration to provide a quantitative measure of patient respiration.

8 Claims, 4 Drawing Figures

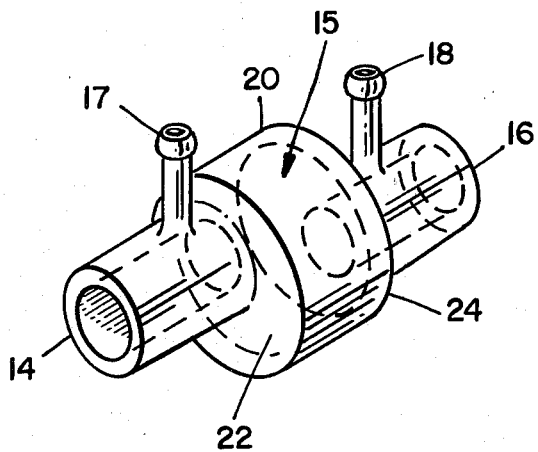
FIG_1
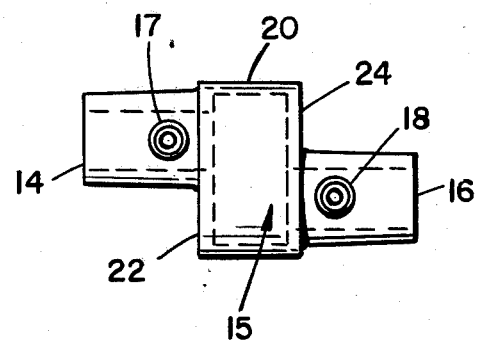
FIG_2
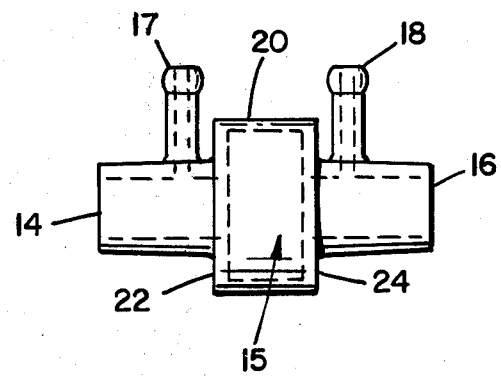
FIG_3
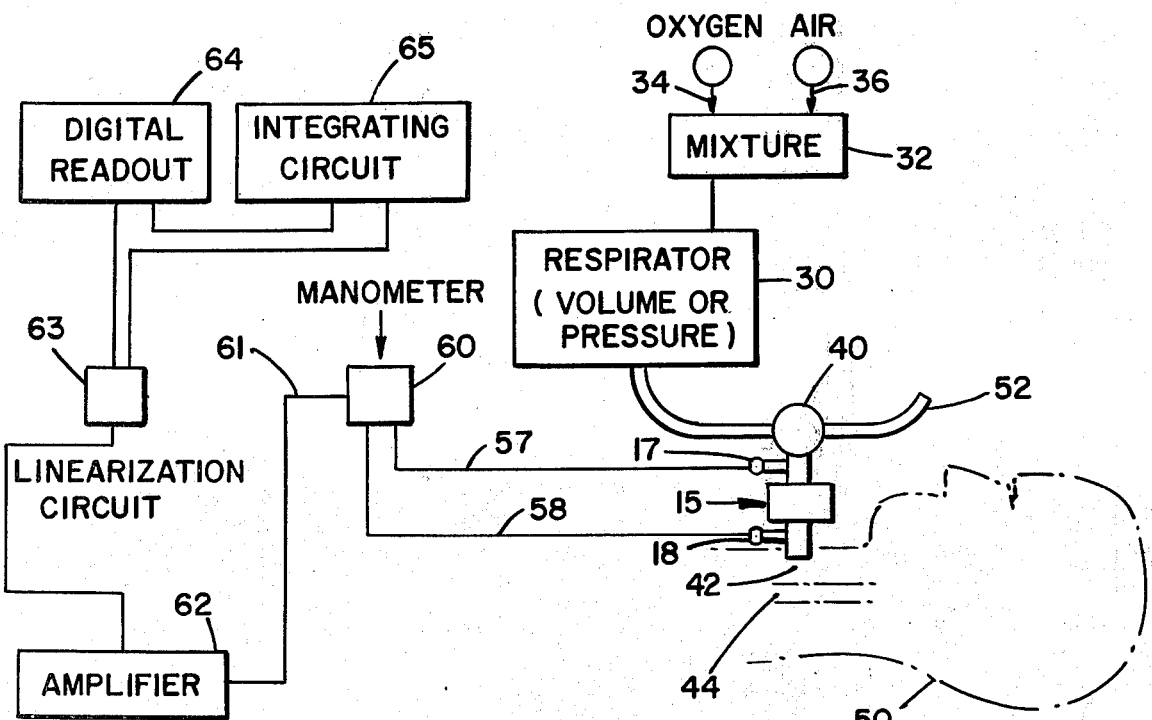
FIG_4

AIR FLOW TO PRESSURE DIFFERENTIAL TRANSDUCER FOR PNEUMOTACHOGRAPHY

The invention described herein was made in the course of work under a grant or award from the Department of Health, Education and Welfare.

This invention relates to an air flow to pressure differential transducer for use in pneumotachography.

SUMMARY OF THE PRIOR ART

Heretofore, pneumotachographs have consisted of a matrix of small parallel passages placed interiorly of a large volume. This matrix of small parallel apertures typically communicates air to and from a patient by being placed within an endotracheal tube. The purpose of the small parallel passages is to produce a laminar flow of air which produces a pressure drop that is linearly related to the fluid flow rate to and from a patient. Typically, the pressure drop has been measured at one or more of the discrete small parallel passages.

Such devices have heretofore had severe limitations. Typically, their usefulness is restricted to cardioplumonary function laboratory conditions. This has occurred primarily because of plugging or clogging of the parallel passages. This plugging or clogging is encountered when such devices have been used for measurements on actual endotracheal tubing in patients during treatment such as that provided for patients with severe cardio-pulmonary disease and other conditions encountered in an intensive care unit of a hospital.

This clogging occurs through either the presence of condensation from the saturated inspirated or expirated gases or, alternately, from the ambient mucus in the patient's breath. Where some of such small parallel passages are obstructed, the flow through the remaining passages changes even to the point where it becomes dangerously restricted to total flow. Where the passage at which the pressure differential measurement occurs becomes unobstructed, dramatically erroneous measurements have resulted.

In an effort to prevent such clogging, the parallel passages have been heated. This, however, has produced a variety of additional complications.

First, where the passages are heated, bulk and weight are added to the endotracheal tubing to the patient with the result that the device becomes heavier, hot and of such a size that it is not conveniently immediately juxtaposed to the patient. Moreover, heating generates a greater gas viscosity which in turn produces a further error in the desired flow rate measurement. Finally, particles of mucus in contact with such heated parallel passages are subject to a protein frying effect which results in solid particles which block and otherwise obstruct the passages.

SUMMARY OF THE INVENTION

A pneumotachograph having an improved air flow to pressure differential transducer is disclosed for producing a pressure differential during inspiration and expiration of respirative air to and from a hospital patient. Typically, the air flow to pressure differential transducer is attached to endotracheal tubing between the patient's trachea and the respirator valve. Specifically, the transducer provides the endotracheal tube with an enlarged and typically cylindrical volume having offset air passages communicating to the endotracheal tube. The unit area of the measuring chamber is greater than the unit area of the communicated endotracheal tubing and is typically cylindrical with respect to such tubing. Typically, the area of the communicated endotracheal tube is preferably less than one quarter the cross-sectional area of the chamber. The endotracheal tubings are preferably offset so that their respective air flows are not in line and the generated air flow interior of the volume is turbulent but not circuitous. Both the communicated endotracheal tubings are provided with manometer taps substantially normal to the path of fluid flow therein so that pressure differential and not velocity head of the fluid flow is measured. Flow through the device is proportional to the differential pressure raised to the 0.57 power. The manometer taps are communicated to a differential pressure transducer. The output of this transducer passes to a linearization circuit to produce a measure of intake and outflow during the patient's respective inspiration and expiration to provide a quantitative measure of patient respiration.

OBJECTS AND ADVANTAGES OF THE INVENTION

It is an object of this invention to disclose a pneumotachograph air flow to pressure differential transducer having a single large non-obstructable channel which can be used during patient care to measure respiration. According to this aspect of the invention, a large flow volume is placed in the endotracheal tubing of a patient. Thus, unit area of the channel is greater than the unit area of the tubing and has its endotracheal apertures aligned for the generation of non-circuitous turbulent flow within the enlarged volume. The unit area of the endotracheal tubing is less than one quarter the cross-sectional area of the chamber.

An advantage of the air flow to pressure differential transducer is that it is not restricted to laboratory conditions where the plugging of numerous parallel restricted apertures can be controlled. Rather, the single large volume through which the fluid is passed is capable of receiving and entrapping fluids during respiration without generating appreciable changes in the desired pressure differential output of the transducer. The transducer can be used in a hospital on patients for measurement of respiratory functions.

A further advantage of the air flow to pressure differential transducer is that internal heating to reduce wetness is not required and protein frying is eliminated.

A further advantage of the air flow to pressure differential transducer is that it is of a weight and bulk amenable for attachment to endotracheal tubing. Where required installation is immediate the throat or mouth of a patient, minimum bulk of the measuring transducer permits convenient attachment.

A further advantage of the air flow to pressure differential transducer is that the device can be readily made in a disposable form. It can be vended in sealed, sanitary containers, opened and used on a patient, and thereafter discarded.

A further advantage of the air flow to pressure differential transducer is that it can be uniformly made so that the flow to differential pressure characteristic is essentially identical for each similarly sized unit.

A further object of this invention is to disclose an air flow to pressure differential transducer for use in pneumotachography which can capture liquids during respiration. According to this aspect of the invention, the expanded volume is made of cylindrical shape. The endotracheal tubes are offset one with respect to another so that their direct flow paths are not coincident and each of the flow paths impacts an adjacent chamber wall. Typically, the endotracheal tubes are aligned so that recessed liquid receiving area is defined interior of the chamber volume.

An advantage of this aspect of the invention is that the device, instead of being required to be kept free of liquids such as water, mucus or the like, can actually accommodate entrapped liquids to some degree (up to one quarter of its volume). This accommodation occurs without appreciable change in the pressure differential output of the transducer.

An advantage of this aspect of the invention is that the transducer conforms to the wet environment of respiration. It is not required that the wet environment be either unsaturated, cleared of mucus and liquid particles or, alternately, that heating occurs. Consequently, instruction and operation of the transducer is vastly simplified.

Yet another object of this invention is to disclose an air flow to pressure differential transducer which produces minimum high frequency noise. According to this aspect of the invention, the endrotracheal tubes communicate normally to the enlarged cylindrical chamber at offset, parallel and non-intercepting flow paths. By maintaining the unit inlet areas at less than one quarter of the unit chamber area, high frequency noise that can interfere with attached manometers is attenuated.

A further advantage of this invention is that airway pressure is communicated to the measuring manometer by low restrictive paths and that tuning of the measuring manometer circuit to reject erroneous common mode pressure can occur.

Yet a further object of this invention is to demonstrate an operative connection of such a pneumotachograph transducer to electronic circuitry for linearization and integrating patient respiration during treatment.

Other objects, features and advantages of this invention will become more apparent after referring to the following specification and attached drawings in which:

FIG. 1 is a perspective view of an air flow to pressure differential transducer of this invention;

FIG. 2 is a view of the transducer in top plan;

FIG. 3 is a side elevation of the transducer; and,

FIG. 4 is a simplified schematic of the transducer connected to the tracheal passage of a patient assisted in breathing through a conventional respirator.

Referring to FIG. 1, a first cylindrical endotracheal tube 14 is shown communicating inwardly to a central expansion volume 15. A second cylindrical endotracheal tube 16 communicates from the expansion volume 15. Expansion volume 15 is cylindrical, having a cylindrical sidewall 20 and two circular endwalls 22, 24. First cylindrical endotracheal tube 14 communicates through circular endwall 22; second cylindrical endotracheal tube 16 communicates through circular endwall 24.

Paired manometer taps 17, 18 are provided. These manometer taps measure the pressure in the respective endotracheal tubings 14, 16. They are aligned normal to the passage of air within tubings 14, 16. In this way they measure pressure only; velocity head is not measured.

Comparing inlet tube 14 as connected to circular wall 22, with inlet tube 16 as connected to circular wall 24, it will be noted that both of the respective tubes and circular walls are precisely identical. Thus, by the manufacture of a single circular wall and cylindrical tube, together with manometer outlet taps, both end walls of volume 15 can be made. Moreover, by providing an enlarged cylindrical tube 20, and respective sealing mechanisms, typically between the interior of the wall 20 and the exterior of the circular walls 22 and 24, the respective end walls of the transducer can be moved in trombonelike movement towards and away from one another. The volume 15 can thus be changed.

Referring to FIGS. 2 and 3, further analysis of the important positioning of the inlet and outlet tubes 14 and 16 may be observed. It will be noted that tube 14 is offset with respect to tube 16. Specifically, flow through tube 14 will impinge upon wall 24 and will not pass directly to tube 16. Likewise, flow through tube 16 will impinge upon wall 22 and not flow directly into tube 14. This aspect of the invention can plainly be seen in the plan view of FIG. 2.

With respect to FIG. 3, it will be noted that flow through either tube 14 or 16 clears the lowest portion of the interior volume 15 by a preselected interval constituting approximately one quarter the volume of chamber 15. This preselected lower volume below the tubings 14, 16 enables the transducer of this invention to accumulate fluids inevitably present in respiration. It has been found that the respirated fluids accumulated within the volume 15 do not appreciably effect pressure differential across the manometer taps 17, 18. This ability to accumulate respirated fluids is a highly advantageous aspect of this invention which allows its use in actual patient care rather than in controlled laboratory conditions.

Referring to FIG. 4, the use of this apparatus in pneumotachography is illustrated. Typically, a respirator 30 (either of the volumetric or pressure type) provides respiration through a mixing device 32 with a programmed mixture of oxygen from an oxygen inlet 34, and air or other gas mixtures from inlet 36. The output of the respirator passes to a conventional respirator valve 40. The respirator valve 40 communicates through endotracheal tubing 42 to the trachea 44 of a patient 50. Respirated mixture from the patient is discharged to the atmosphere or a pressure sightly higher through an outlet conduit 52 by function of the conventional respirator valve 40 upon expiration.

As has been set forth, the transducer of this invention which constitutes the enlarged volume 15 is positioned between the respirator valve 40 and the tracheal passage of the patient 44 in the endotracheal tube 42. As is conventional, communication of the endotracheal tube 42 to the trachea 44 of the patient is made by way of a tracheotomy.

The manometer taps 17, 18 are communicated through tuned manometer conduits 57, 58 to a resistance type pressure transducer having a Wheatstone bridge balancing circuit. This manometer 60 has an electrical output 61. Manometers of the type suitable for use with this invention are made by the Stathan Instrument Co. of Oxnard, Cal. and are sold under Model No. PM5-350. Other suitable and similar pressure transducers are available from a number of manufacturers.

Typically, the electrical output from transducer 61 is amplified by amplifier 62 and communicated to a programable multifunction module in the form of a linearization circuit 63. Such linearization circuits can be constructed by those skilled in the art using the programmable multifunction module Model No. 433J, manufactured by Analog Devices of Norwood, Mass.

Thereafter, the linearized outputs can be channelled to either a conventional galvanometer or recorder scaled in an empirically determined scale, or alternately to conventional digital readout circuits such as that illustrated at 64.

Reference has heretofore been made to the tuning of the manometer conduits 57, 58 to the pressure manometer 16 of the resistance type. Such tuning is in the prior art but can be herein briefly explained.

Specifically, tubes 57 and 58 are preferably greater than ⅛ inch diameter. These tubes are communicated to the manometer. By the expedient of communicating both tubes to either one of the manometer taps 17 or 18 and applying normal respirator driving pressure, accurate tuning of the manometer connections can occur. Such tuning of the manometer connections is typically made by adding greater or lesser lengths of manometer tubing 57, 58 between the volume 15 until the integrated output approaches a zero reading over a respiratory cycle.

Thereafter, and in operation of the transducer, the tubes are connected across the manometer taps 17, 18 and linearization of the pressure differential commenced at the circuits to indicate respiratory flow. Integration commences to indicate respiratory volume.

It should be appreciated that in the type of device here shown, especially for pneumotachography of a patient, the range of physiological air flow varies greatly depending on the patient's age, size and life support parameters. Therefore, the actual physical dimensions of the transducer of this invention will vary depending on the range of flow to be measured. Because of this dependence, the actual physical dimensions of the transducer set forth here are identified with an average adult.

Typically, the tubings 14, 16 are preferred to be ⅜ inch inside diameter and are sized at the outside to be 0.620 inch on a 1° taper from their ends so that actual connection to standard endotracheal tubing can occur. These tubes have a unit inlet flow area of less than one quarter the cross-sectional area of the expansion volume 20.

The pressure manometer taps are ⅛ inch or larger, inside diameter at the respective taps 17, 18. It has been found preferable to make these pressure taps ⅛ inch diameter. Dimension of the pressure manometer taps below one eighth inch are not preferred because restrictive effect within the tubes causes tuning of their connection to the pressure manometer 60 to become extremely critical to the point where operative accurate measurement is not possible.

The wall 20 is provided with an inside diameter that is approximately 1 inch. It has been found that this is an optimum dimension. A dimension below three quarters of an inch is not preferred unless smaller area inlet tubing is used.

The spatial separation between the inside of walls 22, 24 within the cylindrical wall 20 is likewise important. Specifically, the separation at a minimum must be such that the overall pressure drop will not cause discomfort or impaired breathing to the patient. It has been found empirically that distances between walls of less than one quarter inch produce an intolerable pressure drop.

The maximum separation of the wall should not exceed three quarters of an inch. This is because the dead space between the patient and respirator becomes too large. The preferred dimension between the inside dimension of walls 22, 24 is one half inch.

Thus, the preferred dimensions of the chamber are ⅜ inch diameter for the endotracheal tubes, 1 inch diameter for the cylindrical volume therebetween, one half inch between the two end walls, and ⅛ inch diameter for the two manometer taps.

Further, it will be seen that the preferred axis of the endotracheal tube connected to chamber 20 is offset by at least an amount equal to its diameter. Moreover, it will be seen that the distance between walls 22 and 24 is large enough to not impair breathing and small enough to not introduce intolerable dead space.

Assuming that a transducer is made according to the preferred dimensions set forth above, the air flow as corresponded to pressure differential in millimeters of water can be equated to the following table:

| ROOM AIR FLOW THROUGH THE DEVICE AT 1 ATM, 70°F IN LITERS PER MINUTE | DIFFERENTIAL PRESSURE BETWEEN TUBE A AND C IN MM $H_2O$ |
|---|---|
| 95 | 42 |
| 85.5 | 32 |
| 74 | 20 |
| 67.5 | 16 |
| 57 | 12 |
| 47.5 | 8 |
| 38 | 6 |
| 28.5 | 4 |
| 19 | 2 |
| 9.5 | 1 |

It will be noted that the pressure differential is substantially non-linear with respect to fluid flow. It has been found with reference to a log-log plot by plotting the above empirically determined information that air flow ($F$) is approximately equal to the product of a constant ($K$) and the pressure differential ($\Delta P$) across the manometer taps 17, 18. The equation is $F \approx K(\Delta P)^{0.57 \pm 0.1}$. For a transducer made according to the dimensions set forth above, the constant $K$ is approximately 3.16.

Theoretical treatments of non-uniform flow which are believed to occur within this flow meter may be highly developed in some fields, such as fluid amplifiers. However, the theoretical description of fluid flow within the device here shown has not been attempted. The preferred dimensions and parameters have all been empirically determined and are dictated by the range of physiological air flow and patient safety. The generation of a satisfactory theoretical treatment of fluid flow within the impact flow meter transducing volume is not determined.

It should be apparent that this invention will admit of modification. For example, the device will obviously work with other than a tracheal connection. Additionally, the expansion volume could be other than cylindrical. Moreover, the inlet and outlet conduits do not have to be in parallel flow. It is sufficient if they produce a non-circuitous, non-intercepting path into the expanded volume which provides some volume for the capture of respirated fluids such as condensed water and mucus. Further, the size of the device can be expanded or contracted providing the parameters herein disclosed are preserved. Within the range of physiological air flow and as dimensional and shape changes are made to the transducer within the framework above, the constant $K$ of the flow $F$ equation $F \approx K(\Delta P)^{0.57}$ will increase or decrease while the factor of differential pressure to the 0.57 power remains approximately the same. Likewise, other modifications may be made without departing from the spirit and scope of this invention.

We claim:

1. An improved air flow to pressure differential transducer adapted to be used by a patient comprising a chamber having at least one sidewall closed by two end walls and enclosing therein a predetermined volume, the distance between said end walls being such that the airflow to or from a patient is normal, said chamber defining an unobstructed volume therewithin; first and second air passages each transpiercing one of said end walls for the flow of air into and out of said chamber across said unobstructed volume, said air passages having axes of flow offset by an amount equal to or greater than their cross-section at said chamber and each having a unit area equal to or less than one quarter the cross-sectional area of said chamber; and, first and second manometer taps for measuring the pressure differential of fluid flow between said passages across said chamber, said first manometer tap connected to said first passage and said second manometer tap connected to said second passage.

2. The invention of claim 1 and wherein said air passages are offset with respect to said unobstructed chamber so that flow through each passage impinges upon an end wall of said chamber.

3. The invention of claim 1 and wherein said volume interior of said chamber defines a fluid collection area.

4. The invention of claim 1 and wherein said chamber is cylindrical.

5. The invention of claim 1 and wherein said first and second air passages communicate to said chamber along parallel, non-intersecting flow paths.

6. An improved pneumotachograph including the combination of a respirator; an air passage connected to said respirator and adapted to communicate air from said respirator to a patient; an air flow to pressure differential transducer connected to the passage and adapted to be across the air flow from said respirator to said patient; and, linearization, integrating and flow readout circuits operatively connected to said pressure differential transducer providing electrical signals indicative of the respiration of said patient, the improvement in said air flow to pressure differential transducer comprising: a chamber having at least one sidewall closed by two end walls and enclosing therein a predetermined volume, the distance between said end walls being such that the airflow to or from a patient is normal, said chamber defining an unobstructed volume therewithin; first and second air passages each transpiercing one of said end walls for the flow of air into and out of said chamber across said unobstructed volume, said air passages at said end walls having axes of flow offset by an amount equal to at least their cross-section at said chamber and each having a unit area equal to or less than one quarter the cross-sectional area of said chamber; and, first and second manometer taps for measuring the pressure differential of fluid flow between said passages across said chamber, said first manometer tap connected to said first passage, and said second manometer tap connected to said second air passage, said taps being operatively connected to said circuits.

7. An improved air flow to pressure differential transducer adapted to be used by a patient comprising: a chamber enclosing therein a predetermined unobstructed volume; first and second air passages transpiercing the walls of said chamber for the flow of air into and out of said chamber across said unobstructed volume, the distance between the walls at the points where the passages transpierce them being such that the airflow to or from a patient is normal, said first and second air passages aligned with respect to the volume of said chamber for impact of air inflow through one passage upon a wall of said chamber rather than upon the opening for the remaining air passage, said passages having a unit area equal to or less than one quarter the cross-sectional area of said chamber; and, first and second manometer taps for measuring the pressure differential of fluid flow across said chamber with said first manometer tap connected to said first passage and said second manometer tap connected to said second passage, and, where flow rate through said chamber is proportional to the product of a constant and the pressure differential raised to the 0.57 ± 0.1 power.

8. An improved air flow to pressure differential transducer comprising: a cylindrical chamber having a diameter greater than one half inch; two circular end walls closing said cylindrical chamber at either end, the distance between said end walls being between one quarter inch and three quarters of an inch, said chamber defining an unobstructed volume therewithin; first and second passages each transpiercing one of said end walls to permit airflow into and out of said chamber across said unobstructed volume, said air passages each aligned with respect to the unobstructed volume of said chamber for impact of air inflow through one passage upon a wall of said chamber rather than upon the opening for the remaining air passage, said passages having a unit area equal to or less than one quarter the cross-sectional area of said chamber; and, first and second manometer taps at said passages each having an interior diameter equal to or greater than one eighth inch for measuring the pressure differential of fluid flow across said chamber, said first manometer tap connected to said first passage and said second manometer tap connected to said second passage.

* * * * *